(12) United States Patent
Anshel et al.

(10) Patent No.: US 7,649,999 B2
(45) Date of Patent: Jan. 19, 2010

(54) METHOD AND APPARATUS FOR ESTABLISHING A KEY AGREEMENT PROTOCOL

(76) Inventors: Iris Anshel, 31 Peter Lynas Ct., Tenafly, NJ (US) 07670; Michael Anshel, 1140 Fifth Ave., Apt. 3C, New York, NY (US) 10128; Dorian Goldfeld, 31 Peter Lynas Ct., Tenafly, NJ (US) 07670

(*) Notice: Subject to any disclaimer, the term of this patent is extended or adjusted under 35 U.S.C. 154(b) by 772 days.

(21) Appl. No.: 11/148,748

(22) Filed: Jun. 8, 2005

(65) Prior Publication Data

US 2006/0280308 A1 Dec. 14, 2006

(51) Int. Cl.
*H04L 9/00* (2006.01)
(52) U.S. Cl. .................................................... 380/285
(58) Field of Classification Search .............. 380/44, 380/255, 278, 285, 46, 30
See application file for complete search history.

(56) References Cited

U.S. PATENT DOCUMENTS

| | | | |
|---|---|---|---|
| 6,023,689 A | 2/2000 | Herlin et al. | |
| 7,000,110 B1* | 2/2006 | Terao | 713/172 |
| 2003/0081785 A1 | 5/2003 | Boneh et al. | |
| 2004/0083368 A1 | 4/2004 | Gehrmann | |
| 2005/0018841 A1 | 1/2005 | Girault | |

OTHER PUBLICATIONS

Shahram Siavash, Monoids Homomorphism, Formalized in BESTT, CAS 701 Presentation, Dec. 5, 2002 Department of Computing and Software, McMaster University, Retrieved date Nov. 30, 2008 http://imps.mcmaster.ca/courses/CAS-701-02/contributions/homomorphisms.pdf.*
R. P. Hunter, "On certain Two Generator Monoids" 1993 Springer-Verlag New York Inc. Semigroup Forum vol. 47 (1993) 96-100 http://www.springerlink.com/content/7p14183p7Iq70135/fulltext.pdf Retrieved date Nov. 30, 2008.*
International Search Report and Written Opinion for PCT Application PCT/US2006/22483, mailed Sep. 11, 2007, 8 pages.

* cited by examiner

*Primary Examiner*—Jung Kim
*Assistant Examiner*—Samson B Lemma
(74) *Attorney, Agent, or Firm*—Steven S. Rubin; Dilworth & Barrese

(57) ABSTRACT

A system and method for generating a secret key to facilitate secure communications between users. A first and second and a function between the two monoids are selected, the function being a monoid homomorphism. A group and a group action of the group on the first monoid is selected. Each user is assigned a submonoid of the first monoid so that these submonoids satisfy a special symmetry property determined by the function, a structure of the first and second monoids, and the action of the group. A multiplication of an element in the second monoid and an element in the first monoid is obtained by combining the group action and the monoid homomorphism. First and second users choose private keys which are sequences of elements in their respective submonoids. A first result is obtained by multiplying an identity element by the first element of the sequence in a respective submonoid. Starting with the first result, each element of the user's private key may be iteratively multiplied by the previous result to produce a public key. Public keys are exchanged between first and second users. Each user's private key may be iteratively multiplied by the other user's public key to produce a secret key. Secure communication may then occur between the first and second user using the secret key.

8 Claims, 11 Drawing Sheets

METHOD AND APPARATUS FOR ESTABLISHING A KEY AGREEMENT PROTOCOL

BACKGROUND OF THE INVENTION

1. Field of the Invention

The invention relates to cryptography and, more particularly, to a system and method for facilitating cryptographic applications.

2. Description of the Prior Art

Key Agreement Protocols

It is sometimes desirable for individuals to be able to communicate with each other in a way in which third parties are unable to listen to the communication. A simple way for these individuals to communicate is to have the communications themselves proceed in private. For example if party A and party B desire to communicate in a way which will not be heard by party C, A and B can simply meet at a designated location unknown to C. Similarly, A and B can set up a designated communication line between them which excludes C. Such communication lines are expensive and inconvenient especially if A and B are geographically far apart from one another.

A first approach to facilitating private communications between A and B is to give A and B a secret key that may be used to encrypt and/or decrypt messages sent between A and B. If C does not know what the key is, it may be very difficult for C to both get a hold of a message sent between A and B and try to understand it. However, giving A and B such a key is also cumbersome, expensive and time consuming. Issues to be addressed include secretly transmitting such a key to A and B and generating a new key each time two individuals need to communicate. Also, if C does ascertain the secret key, then all communications between A and B can be decrypted and read by C.

Another approach for facilitating private communications between A and B is to assign A and B secret mathematical functions $f_a$, $f_b$ respectively. The functions $f_a$ and $f_b$ are chosen from a set of functions, S, all of whose elements are designed so as to be commutative: applying $f_a$ followed by $f_b$ yields the same result as applying $f_b$ followed by $f_a$ (i.e., given an element x, $f_a(f_b(x))=f_b(f_a(x))$). Assuming the element x is known by both A and B, A can then send $f_a(x)$ to B, and B can send $f_b(x)$ to A over public channels. The secret key that can be evaluated and shared by both A and B is then, $f_a(f_b(x))=f_b(f_a(x))$. To insure that the system is secure (from an adversary C who knows x and can listen to all communication between A and B) it is necessary that the functions $f_a$ and $f_b$ satisfy the following property: given the value $f_a(x)$ (respectively $f_b(x)$) it is computationally difficult to determine the function $f_a$ (respectively $f_b$). This is called the general Diffie-Hellman key agreement protocol.

Many specific instances of the general Diffie-Hellman protocol for sending secure communications between A and B are known in the prior art (see Alfred J. Menezes, Paul C. van Oorschot, and Scott A. Vanstone, "Handbook of Applied Cryptography," CRC Press (1997)). They all differ by their choice of the set of functions. The original Diffie-Hellman key agreement protocol is an example of the above described techniques (see W. Diffie and M. E. Hellman, "New directions in cryptography," IEEE Transaction on Information Theory, vol. IT 22 (November 1976), pp. 644-654). Using an algorithm like the one first introduced by Diffie-Hellman, parties A and B can obtain a common shared secret by communicating over a public channel. The security of the system, in this instance, rests on the computational difficulty of computing discrete logarithms in the multiplicative group of the finite field. In more general cases the security is based on the notion of a one-way function. A function $f$ from a set X to a set Y is termed one-way if $f(x)$ is easy to compute for all $x \in X$ but for essentially all elements y it is computationally difficult to find $x \in X$ such that $f(x)=y$. To date a diverse array of mathematical techniques (including geometric and algebraic ones), have been used to create systems for secure communication whose security is based on one-way functions.

A problem with some of the prior art algorithms, is that most of them rely on a cost-risk analysis when generating the one-way function. That is, in order to produce a more complex and more difficult to determine secret key, each party would need to spend more time in generating such a key and may need to invest in more expensive devices. With rapidly evolving technologies, implementing the current algorithms in a cryptographically secure manner is becoming difficult. Furthermore, there are instances of resource limited devices where current algorithms are difficult to implement. Thus, there is a need in the art for a system and method which can produce a secure key relatively quickly and without employing expensive devices.

SUMMARY OF THE INVENTION

An aspect of the invention is a method for securing communications from a user. The method comprises selecting a first monoid, selecting a second monoid and selecting a function, the function being a monoid homomorphism that maps the first monoid to the second monoid. The method further comprises selecting a group, selecting an action of the group on the first monoid, and determining a semi-direct product of the first monoid and the group to produce a third monoid. The method further comprises selecting a first and second submonoid of the third monoid, a pair of the first and second submonoids satisfying a criterion, the first submonoid being defined by a first set of generators, wherein the criterion satisfies a property determined by the function, a structure of the first and second monoids, and the action. The method still further comprises selecting a plurality of generators of the first set of generators to produce a private key.

Another aspect of the invention is a method for securing communications from a user. The method comprises receiving a first submonoid, the first submonoid being produced by selecting a first monoid, selecting a second monoid, selecting a function, the function being a monoid homomorphism that maps the first monoid to the second monoid, selecting a group, selecting an action of the group on the first monoid, determining a semi-direct product of the first monoid and the group to produce a third monoid, selecting a first and second submonoid of the third monoid, the pair of the first and second submonoids satisfying a criterion, the first submonoid being defined by a first set of generators, the criterion satisfying a property determined by the function, a structure of the first and second monoids, and the action. The method further comprising selecting a plurality of generators of the first set of generators to produce a private key. The method still further comprising applying the second component of an identity on a non-group component of a first generator of the private key to produce a result, wherein the identity comprises a first component, the first component being an identity of the second monoid, and the identity comprises a second component, the second component being an identity of the group. The method still further comprising applying the function to the result to produce a first modified result, multiplying the first component of the identity by the modified result to produce a first further modified result, multiplying the second component of the identity with a group component of the first generator to produce a first still further modified result, and combining the first further modified result with the first still further modified result to produce a public key.

Still another aspect of the invention is a method for securing communications among two users. The method comprises selecting a first monoid, selecting a second monoid, and selecting a function, the function being a monoid homomorphism that maps the first monoid to the second monoid. The method further comprising selecting a group, selecting an action of the group on the first monoid, and determining a first semi-direct product of the first monoid and the group to produce a third monoid. The method still further comprising selecting a first and second submonoid of the third monoid, a pair of the first and second submonoids satisfying a criterion, the first submonoid being defined by a first set of generators, the second submonoid being defined by a second set of generators, the criterion satisfying a property determined by the function, a structure of the first and second monoids, and the action. The method further comprising at a first user, receiving the first submonoid, selecting a plurality of generators of the first set of generators to produce a first private key, and applying the second component of an identity on a non-group component of a first generator of the first private key to produce a first result, wherein the identity comprises a first component, the first component being an identity of the second monoid, and the identity comprises a second component, the second component being an identity of the group. The method further comprising at the first user applying the function to the first result to produce a first modified result, multiplying the first component of the identity by the modified result to produce a first further modified result, multiplying the second component of the identity with a group component of the first generator of the first private key to produce a first still further modified result, and combining the first further modified result with the first still further modified result to produce a first public key. The method still further comprising at the first user a. applying a group component of the first public key on a non-group component of a second generator of the first private key to produce a second result, b. applying the function to the second result to produce a second modified result, c. multiplying a non-group component of the first public key by the second modified result to produce a second further modified result, d. multiplying the group component of the first public key with a group component of the second generator of the private key to produce second still further modified result; and e. combining the first further modified result with the second still further modified result to produce a second public key. The method further comprising at a second user receiving the second submonoid, selecting a plurality of generators of the second set of generators to produce a second private key, applying the second component of the identity on a non-group component of a first generator of the second private key to produce a third result, applying the function to the third result to produce a third modified result, multiplying the first component of the identity by the third modified result to produce a third further modified result, multiplying the second component of the identity with a group component of the first generator of the second private key to produce a third still further modified result and combining the third further modified result with the third still further modified result to produce a third public key. The method still further comprising at the second user f. applying a group component of the third public key on a non-group component of a second generator of the second private key to produce a fourth result, g. applying the function to the fourth result to produce a fourth modified result, h. multiplying a non-group component of the third public key by the fourth modified result to produce a fourth further modified result, i. multiplying the group component of the third public key with a group component of the second generator of the second private key to produce a fourth still further modified result; and j. combining the fourth further modified result with the fourth still further modified result to produce a fourth public key.

Yet still another aspect of the invention is a transmitter comprising a memory including a first submonoid, the first submonoid being produced by selecting a first monoid, selecting a second monoid, selecting a function, the function being a monoid homomorphism that maps the first monoid to the second monoid, selecting a group, selecting an action of the group on the first monoid; determining a semi-direct product of the first monoid and the group to produce a third monoid, selecting a first and second submonoid of the third monoid, the pair of the first and second submonoids satisfying a criterion, the first submonoid being defined by a first set of generators, the criterion satisfying a property determined by the function, a structure of the first and second monoids, and the action. The transmitter further comprising a processor wherein the processor is effective to select a plurality of generators of the first set of generators to produce a private key. The processor is further effective to apply the second component of an identity on a non-group component of a first generator of the private key to produce a result, wherein the identity comprises a first component, the first component being an identity of the second monoid, and the identity comprises a second component, the second component being an identity of the group. The processor is further effective to apply the function to the result to produce a first modified result. The processor is effective to multiply the first component of the identity by the modified result to produce a first further modified result. The processor is effective to multiply the second component of the identity with a group component of the first generator to produce a first still further modified result; and the processor is effective to combine the first further modified result with the first still further modified result to produce a first public key. The processor is effective to a. apply a group component of the first public key on a non-group component of a second generator of the private key to produce a second result, b. apply the function to the second result to produce a second modified result, c. multiply a non-group component of the first public key by the second modified result to produce a second further modified result, d. multiply the group component of the first public key with a group component of the second generator of the private key to produce second still further modified result, and e. combine the first further modified result with the second still further modified result to produce a second public key.

Still another aspect of the invention is a system for securing communications between users. The system comprises a communications center, the communications center effective to select a first monoid, select a second monoid, select a function, the function being a monoid homomorphism that maps the first monoid to the second monoid, select a group, and select an action of the group on the first monoid. The communications center further effective to determine a first semi-direct product of the first monoid and the group to produce a third monoid; and select a first and second submonoid of the third monoid, a pair of the first and second submonoids satisfying a criterion, the first submonoid being defined by a first set of generators, the second submonoid being defined by a second set of generators, the criterion satisfying a property determined by the function, a structure of the first and second monoids, and the action. The system further comprising a first transmitter comprising a memory including the first submonoid and a first processor. The first processor effective to select a plurality of generators of the first set of generators to produce a first private key and apply the second component of an identity on a non-group component of a first generator of the first private key to produce a first result, wherein the identity comprises a first component, the first component being an identity of the second monoid, and the identity comprises a second component, the second component being an identity of the group. The first processor further effective to apply the function to the first result to produce a first modified result, multiply the first component of the identity by the modified result to produce a first further modified result, multiply the second component of the identity with a group component of the first generator to produce a first still further modified result and combine the first further modified result with the first still further modified result to produce a first public key. The first processor is further effective to a. apply a group component of the first public key on a non-group component of a second generator of the private key to produce a second result, b. apply the function to the second result to produce a second modified result, c. multiply a non-group component of the first public key by the second modified result to produce a second further modified result, d. multiply the group component of the first public key with a group component of the second generator of the first private key to produce second still further modified result; and e. combine the first further modified result with the second still further modified result to produce a second public key. The system further comprises a second transmitter comprising a memory including the second submonoid and a second processor. The second processor effective to select a plurality of generators of the second set of generators to produce a second private key, apply the second component of the identity on a non-group component of a first generator of the second private key to produce a third result, apply the function to the third result to produce a third modified result, and multiply the first component of the identity by the third modified result to produce a third further modified result. The second processor further effective to multiply the second component of the identity with a group component of the second generator to produce a third still further modified result and combine the third further modified result with the third still further modified result to produce a third public key. The second processor is further effective to f. apply a group component of the third public key on a non-group component of a second generator of the second private key to produce a fourth result, g. apply the function to the fourth result to produce a fourth modified result, h. multiply a non-group component of the first public key by the fourth modified result to produce a fourth further modified result, i. multiply the group component of the third public key with a group component of the second generator of the second private key to produce fourth still further modified result and j. combine the fourth further modified result with the fourth still further modified result to produce a fourth public key.

DETAILED DESCRIPTION OF THE PREFERRED EMBODIMENT

Figure 10:
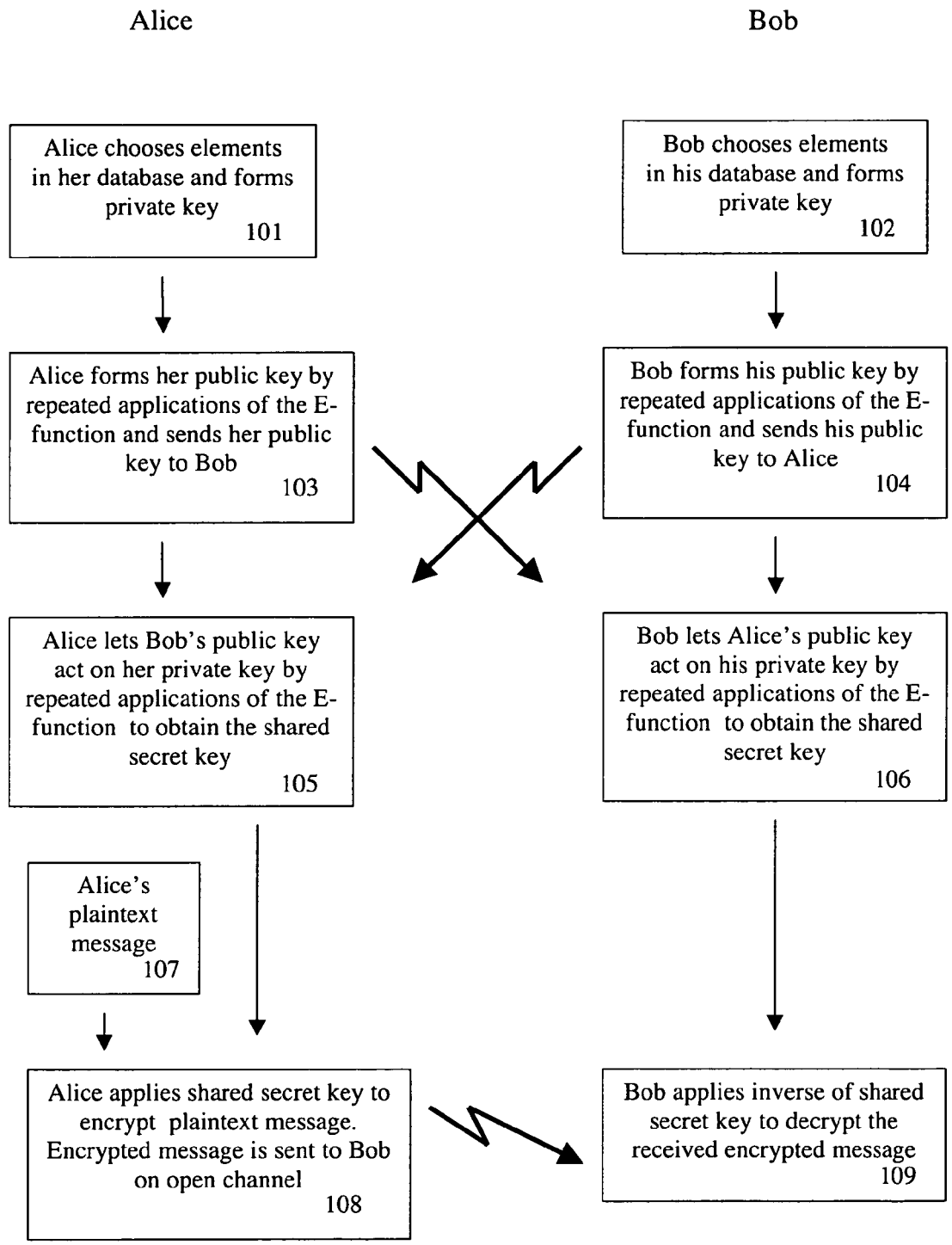
FIG. 10 is a flow diagram illustrating a method for determining a common agreed upon secret key and transmitting a message using that secret key in accordance with an embodiment of the invention.

The present invention introduces an algorithmically efficient one-way function. The algorithm is both rapidly computable and computationally hard to reverse. An overview in accordance with the invention is provided in FIG. 10. Parties Alice and Bob are each in possession of a database from which they form their respective private keys (Boxes 101 and 102). They then proceed to produce their respective public keys based on their respective private keys by applying an algorithm in accordance with the invention (Boxes 103 and 104). Alice and Bob each have access to a respective transmitter and receiver. Alice and Bob use their respective transmitter and receiver to exchange their public keys. By exchanging these public keys they are each in a position to obtain a common agreed upon secret key by letting the received public key act on the respective user's private keys (Boxes 105 and 106). Once the shared secret key has been obtained, Alice can then encrypt a plaintext message, produce an encrypted message (Box 107), send the encrypted message (Box 108) to Bob, who can then decrypt the encrypted message (Box 109) to obtain Alice's plaintext message (Box 107).

Let M, N denote monoids and let S denote a group which acts on M on the left. Given an element $s \in S$, and an element $m \in M$, we denote the result of s acting on m by $^s m$. The semidirect product of M and S, M×S is defined to be the monoid whose underlying set is M×S and whose internal binary operation $$\theta_{M \times S}: (M \times S) \times (M \times S) \to M \times S$$

is given by $$\theta_{M \times S}: (m_1, s_1), (m_2, s_2)) \to (m_1 \cdot {}^{s_1} m_2, s_1 s_2).$$

Furthermore, we let N×S denote the direct product.

An algebraic eraser is specified by a 6-tuple (M×S, N, Π, E, A, B) where M×S and N are as above, A, B are user submonoids of M, Π is an easily computable monoid homomorphism $$\Pi : M \to N,$$

E is a function $$E : (N \times S) \times (M \times S) \to N \times S$$

given by $$E((n,s),(m_1,s_1)) = (n\Pi(^s m_1), ss_1),$$

and A, B are submonoids of M×S such that for all $(a, s_a) \in A$, $(b, s_b) \in B$ $$E((\Pi(a), s_a), (b, s_b)) = E((\Pi(b), s_b), (a, s_a)).$$

Two submonoids satisfying the above identity are termed E-Commuting.

An action of S on M does not induce an action of S on N, and given knowledge of the elements $$(n,s), E((n,s),(m_1,s_1)) \in N \times S$$

it is very difficult to obtain the element $(m_1,s_1) \in M \times S$. The action of the element $s \in S$ has been effectively erased by the algebraic eraser. A benefit lies in the efficiency of the computation of the function Π and the iterative nature of the method and apparatus for the computation of the function E.

A preferred embodiment of an apparatus to perform an algebraic key agreement protocol based on the algebraic eraser, is depicted in FIGS. 1 through 11, and begins with an apparatus to compute the function Π. The Π-Function module 13 is responsive to the data from the Π-Function module library 11, and the input element $m \in M$ from 12. The Π-Function module 13 computes the element $\Pi(m) \in N$.

In general a group S is said to act (on the left) on a monoid M provided there is a homomorphism from S to the endomorphisms of M which satisfies certain properties. Given $s \in S$ and $m \in M$, the element s maps m to a new element in M, denoted $^s m$. The required properties are $$^s(m_1 m_2) = {^s m_1}{^s m_2}, {^1 m} = m, {^{s_1 s_2} m} = {^{s_1}(^{s_2} m)}$$

Figure 1:
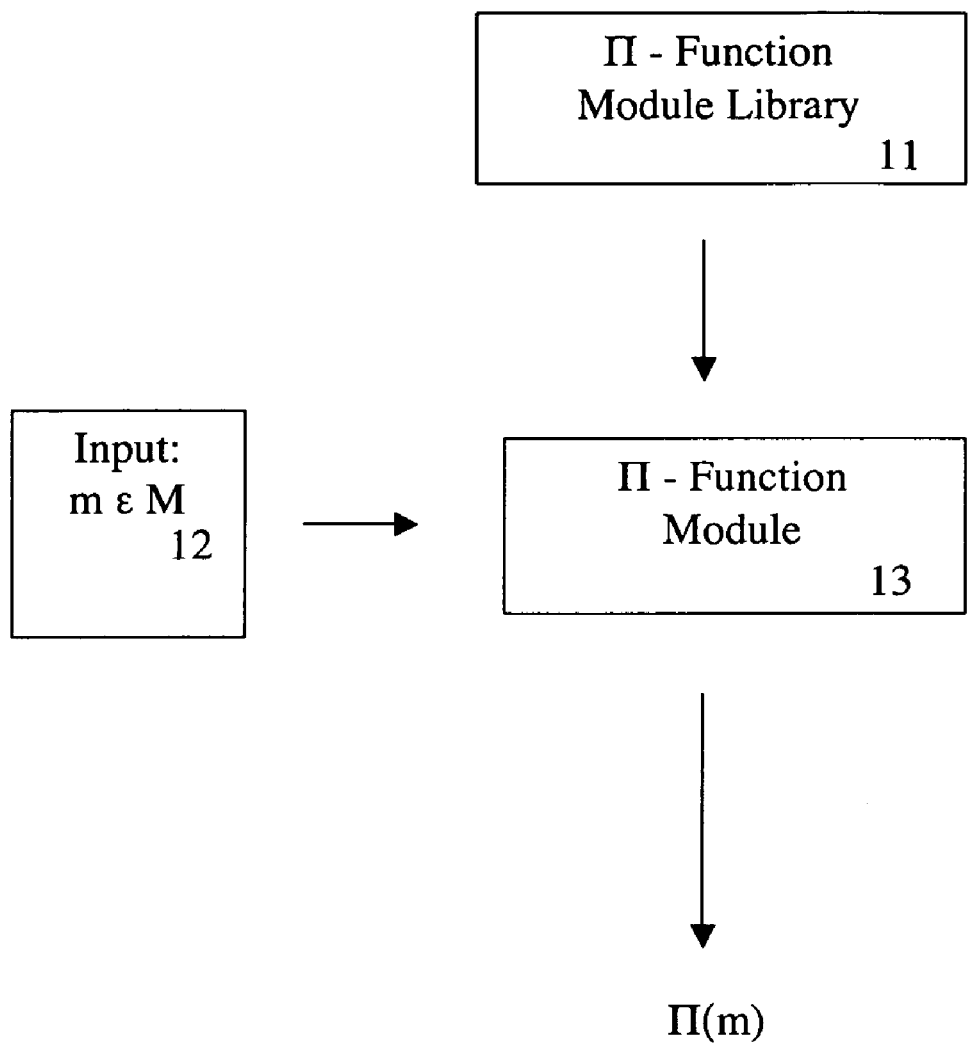
FIG. 1 is a system diagram illustrating a Π-Function module in accordance with an embodiment of the invention.
Figure 2:
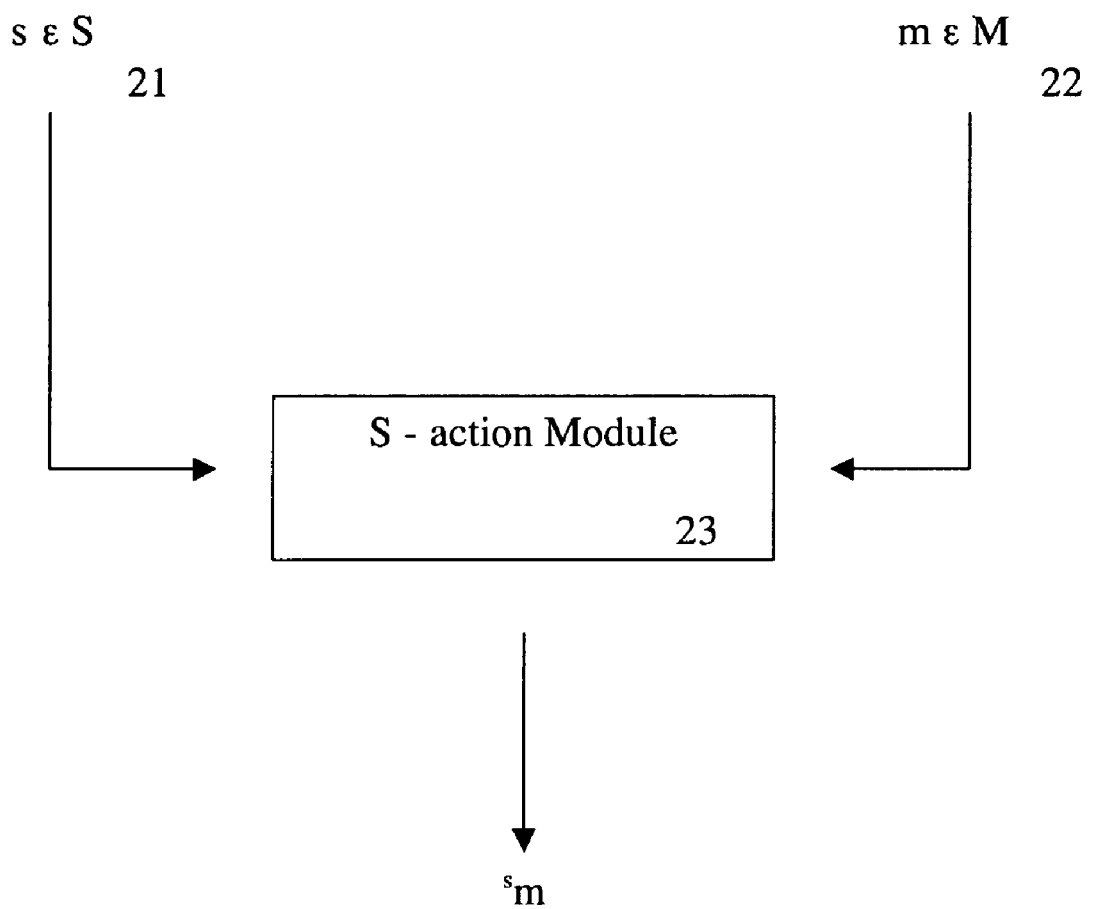
FIG. 2 is a system diagram illustrating a S-Action module in accordance with an embodiment of the invention.

Referring to FIG. 2, S-Action module 23 is responsive to the inputs $s \in S$ 21 and $m \in M$ 22, and computes the image of m under the action of s yielding $^s m$ as output.

Figure 3:
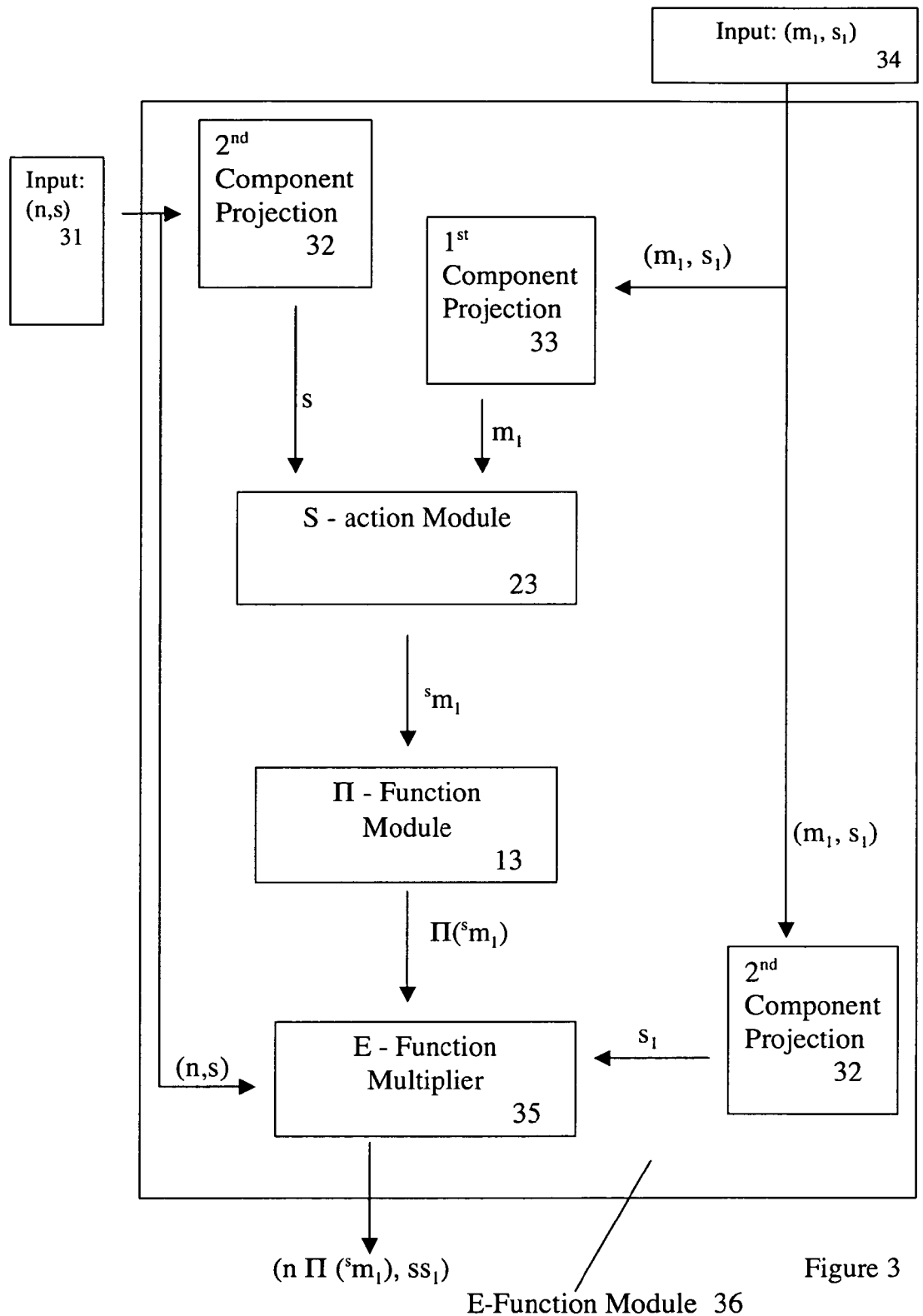
FIG. 3 is a system diagram illustrating an E-Function module in accordance with an embodiment of the invention.

An apparatus to compute the function E is depicted in FIG. 3. The E-Function module 36 is responsive to the inputs (n,s) 31 and (m,s) 34. Given an ordered list (x,y) of two elements x,y, the first component projection of (x,y) outputs the first component x on the list. Similarly, the second component projection outputs the second component y. The input (n,s), 31, is sent to the second component projection module, 32 and the input $(m_1, s_1)$ is likewise sent to a first component projection module, 33. The resulting elements of S and M of the first and second component modules 32, 33 are then forwarded to the S-Action module 23, yielding the element $^s m_1 \in M$. This resulting element $^s m_1$ is forwarded to the Π-Function module, 13, which outputs the element $\Pi(^s m_1)$. The E-Function multiplier, 35, is responsive to the input (n,s), 31, the element $\Pi(^s m_1) \in N$, and the result of the input $(m_1, s_1)$, 34, being entered into the second component projection module, 32. The E-Function multiplier outputs the element $(n \Pi(^s m_1), s_1) \in N \times S$ which is also the output of the E-Function module 36. The semi-direct product of M and S, denoted M×S, is defined to be the monoid whose underlying set is the direct product M×S and whose binary operation is given by $$(m_1, s_1) \cdot (m_2, s_2) = (m_1 \cdot {^{s_1}} m_2, s_1 s_2).$$

It is noted that given an element $(n,s) \in N \times S$ and two elements $(m_1,s_1), (m_2,s_2) \in M \times S$, that $$E((n,s), ((m_1,s_1) \cdot (m_2,s_2))) = E(E((n,s),(m_1,s_1)),(m_2,s_2)).$$

Hence computing the E-Function iteratively increases the system's efficiency and speed.

Figure 4:
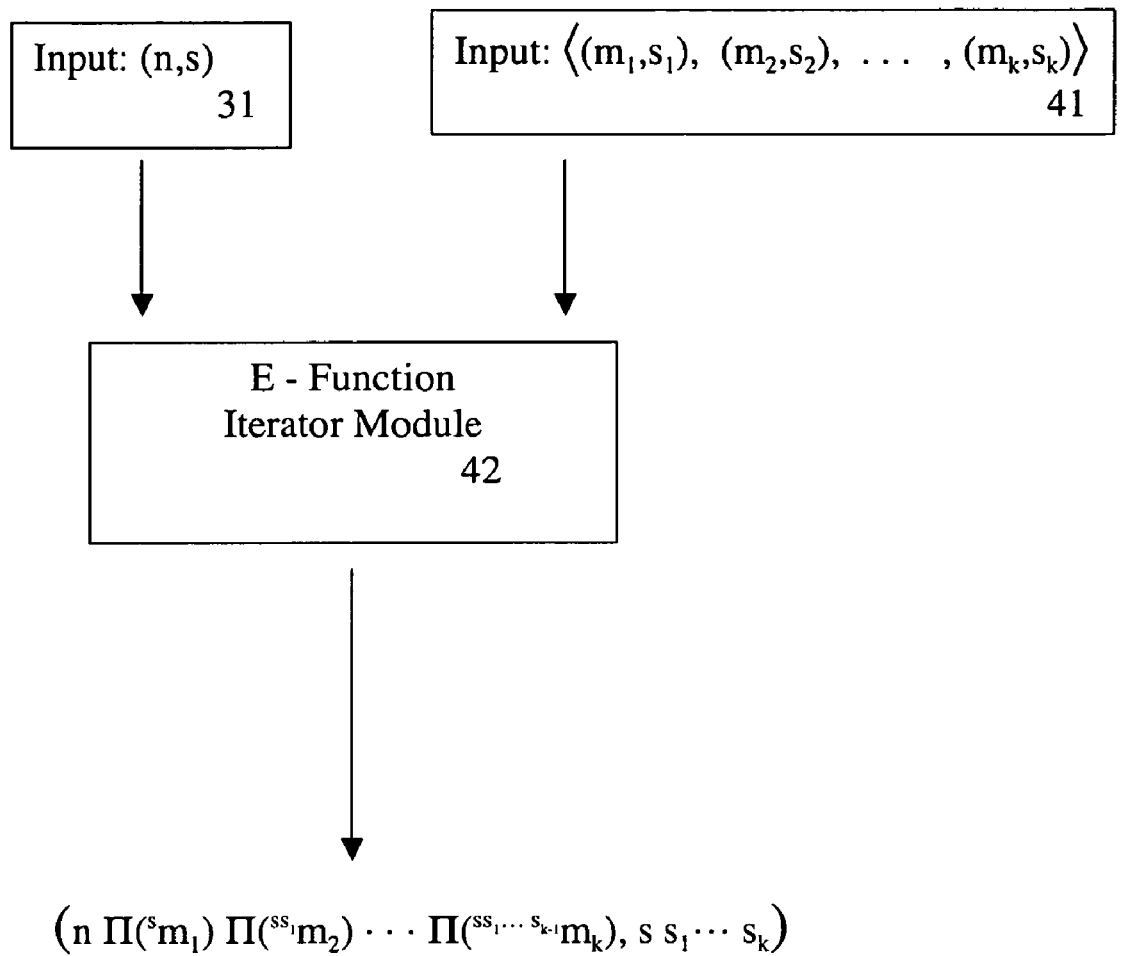
FIG. 4 is a system diagram illustrating the operation of an E-Function iterator module in accordance with an embodiment of the invention.

FIG. 4 depicts an apparatus which may be used in performing the above computation. An E-Function Iterator module 42 is responsive to the input (n,s), 31, and to the input $((m_1,s_1), (m_2,s_2), \ldots, (m_k,s_k))$, 41, and outputs $$(n\Pi(^s m_1)\Pi(^{ss_1} m_2) \ldots \Pi(^{ss_1 \cdots s_{k-1}} m_k), ss_1 \ldots s_k).$$

Figure 5:
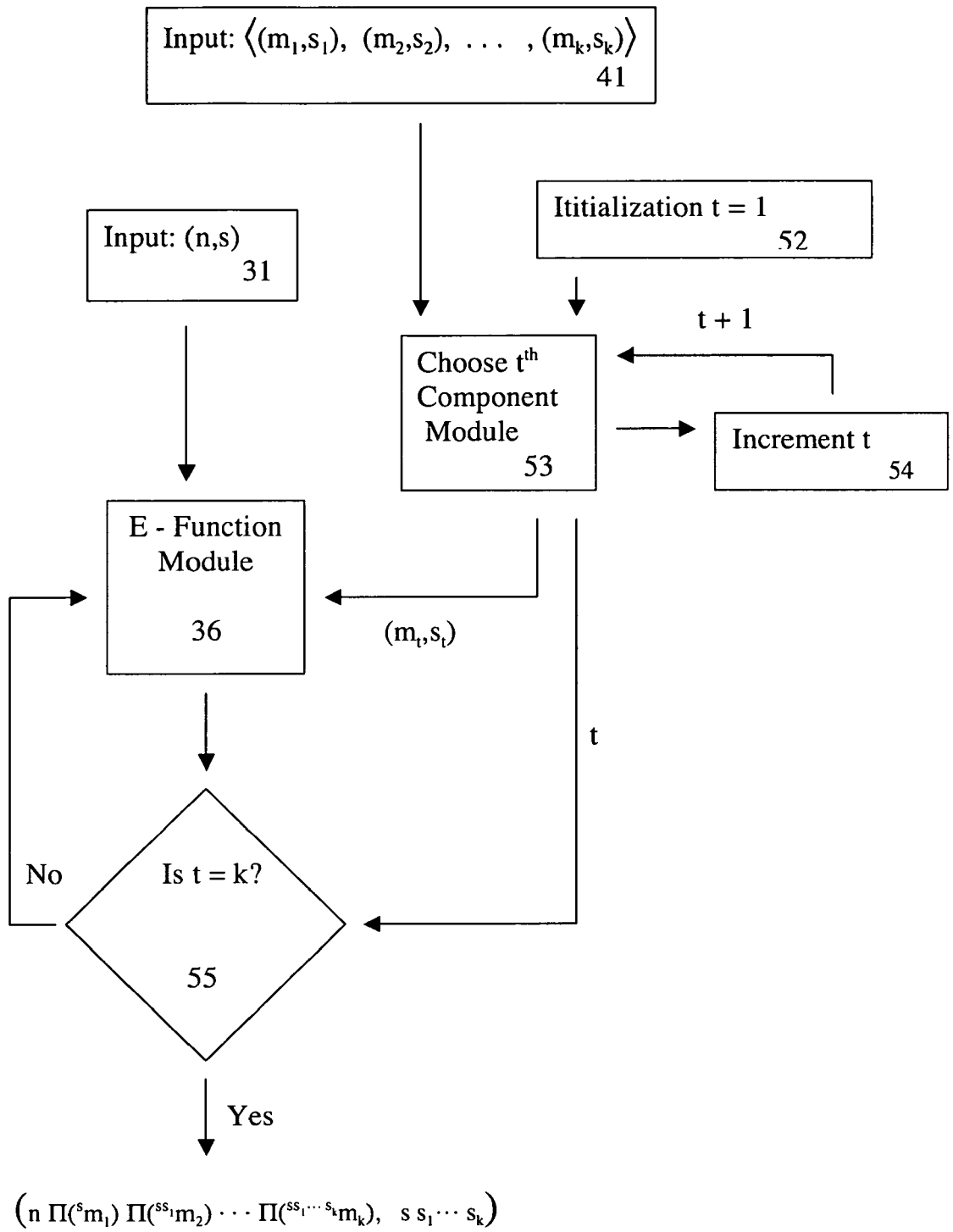
FIG. 5 is another system diagram illustrating the operation of an E-Function iterator module in accordance with an embodiment of the invention.

A more detailed apparatus of the E-Function Iterator module 42, is depicted in FIG. 5, begins with the input (n,s) 31 being sent to the E-Function module 36. In addition, an input $<(m_1,s_1), (m_2,s_2), \ldots, (m_k,s_k)>$, 41, is sent to the choose $t^{th}$ component module, 53, which is a module initialized at the value t=1 and repeatedly incremented by the increment t module, 54. The $t^{th}$ component of the input $<(m_1,s_1), (m_2,s_2), \ldots, (m_k,s_k)>$ is precisely $(m_t, s_t)$ which is the output of 53 and sent to the E-Function module 36. Furthermore the value of t is sent to the decision box 55 which also receives the value of the E-Function (iterated t−1 times up to that point). The decision box 55 determines if t=k, at which point the computation stops, otherwise, the output of decision box 55 becomes input 31 to the E-Function module 36 to be used as the new first component of E together with the incoming entry from choose $t^{th}$ component module 53. The final value arrived at is given by $$(n \cdot \Pi(^s m_1)\Pi(^{ss_1} m_2) \ldots \Pi(^{ss_1 \cdots s_{k-1}} m_k), ss_1 \ldots s_k) = (n \cdot \Pi((^s m_1)(^{ss_1} m_2) \ldots (^{ss_1 \cdots s_{k-1}} m_k)), ss_1 \ldots s_k).$$

Figure 6:
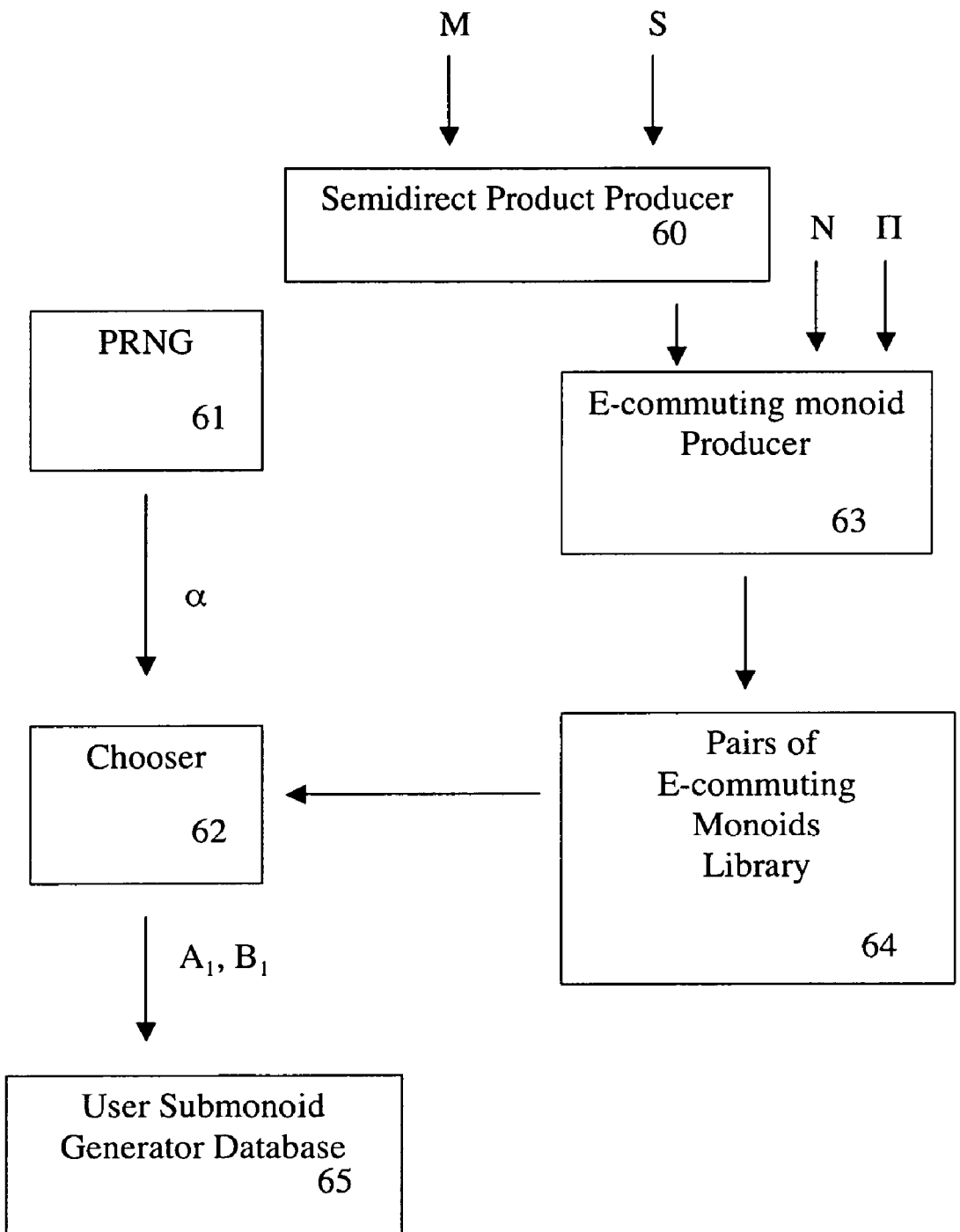
FIG. 6 is a system diagram illustrating a system for determining a pair of E-commuting monoids in accordance with an embodiment of the invention.

Recall that two submonoids A, B are said to be E-Commuting provided $$E((\Pi(a), s_a), (b, s_b)) = E((\Pi(b), s_b), (a, s_a))$$

holds for all $(a, s_a) \in A$, $(b, s_b) \in B$. FIG. 6 illustrates an apparatus which may be used in choosing a pair of E-Commuting monoids, A, B which may be utilized in the invention. A monoid is specified by a generating set, i.e., a subset of elements of the monoid which have the property that every element of the monoid can be expressed as a product of some of these generators (in some order, with repetitions allowed). The Semidirect Product Producer 60 is responsive to the monoid M and the group S and produces the monoid M×S. The monoid M×S, together with the monoid N and the function Π are sent to the E-Commuting Monoid Producer 63, whose output is sent to the Pairs of E-Commuting Monoid Library 64. A Pseudorandom Number Generator 61 produces a random number α, a Chooser 62 then accesses the $α^{th}$ element of the Pairs of E-Commuting Monoid Library 63 and outputs the pair of E-Commuting monoids $A_1, B_1$ which are forwarded to Alice and Bob, respectively. Additionally the pair $A_1, B_1$ is forwarded to the User Submonoid Generator Database 65.

With the apparatuses for computing the S-Action, the functions Π and E specified, and each users submonoid in place, the algebraic eraser key agreement protocol can now be detailed. If the E-commuting monoids $A_1, B_1$, are privately assigned to Alice and Bob, then the invention functions, for example, as a symmetric cryptosystem. If the monoid M×S possesses a large library of pairs of E-Commuting submonoids which are recursively enumerable and whose internal algebraic structure is hidden then the invention can function, for example, as an asymmetric cryptosystem.

Figure 7:
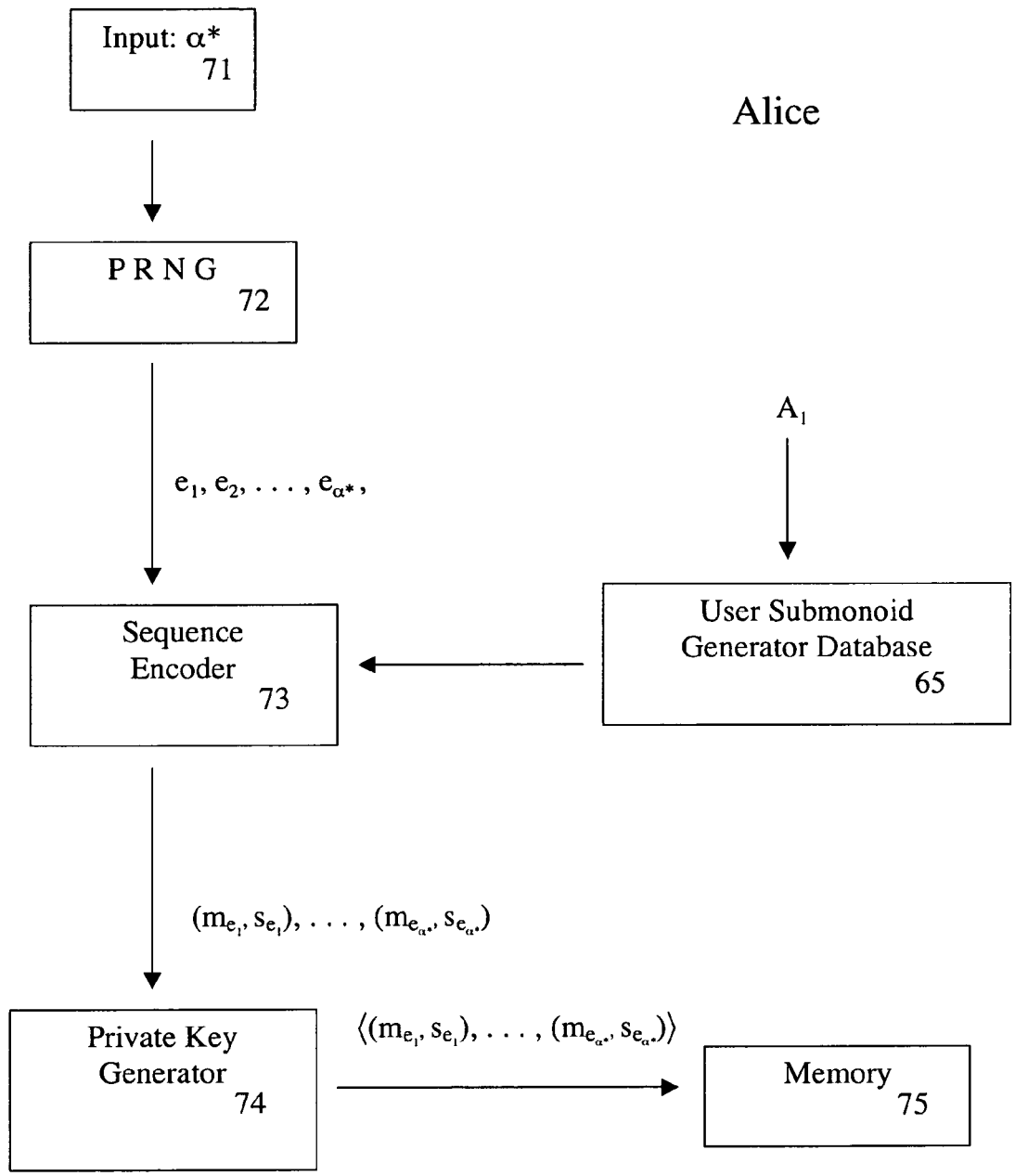
FIG. 7 is a system diagram illustrating a system for determining a private key in accordance with an embodiment of the invention.

FIG. 7 illustrates a mechanism which may be used in enabling a user to generate a private key. Focusing on Alice (Bob case is analogous) a second Pseudorandom Number Generator 72 responsive to the input $\alpha^*$, 71, creates a list of integers $e_1, e_2, \ldots, e_{\alpha^*}$ where each $e_i$ is generated in such a way that $e_i \leq$ number of generators of ($A_1$). The Sequence Encoder 73 is responsive to the list $e_1, e_2, \ldots, e_{\alpha^*}$ and the User Submonoid Generator database 65, is responsive to the submonoid $A_1$. The Sequence Encoder 73 produces the list of the user generators $(m_{e1}, s_{e1}), (m_{e2}, s_{e2}), \ldots, (m_{e_{\alpha^*}}, s_{e_{\alpha^*}})$ out of the generating set of $A_1$. The Private Key Generator 74 is responsive to Encoder 73 and produces the user private key $$(M_A) = <(m_{e1}, s_{e1}), (m_{e2}, s_{e2}), \ldots, (m_{e_{\alpha^*}}, s_{e_{\alpha^*}})>$$

which is sent to a memory 75. It should be observed that the product of the elements, denoted $(M_A, s_A)$, $$(M_A, s_A) = (m_{e_1}, s_{e_1}) \cdot (m_{e_2}, s_{e_2}) \cdots (m_{e_{\alpha^*}}, s_{e_{\alpha^*}})$$
$$= ((m_{e_1})(^{s_1}m_{e_2}) \cdots (^{s_1 \cdots s_{\alpha^*-1}}m_{e_{\alpha^*}}), s_{e_1} \cdots s_{e_{\alpha^*}})$$

is an element of the submonoid $A_1 \subseteq M \times S$, but need not be computed explicitly for key agreement.

Figure 8:
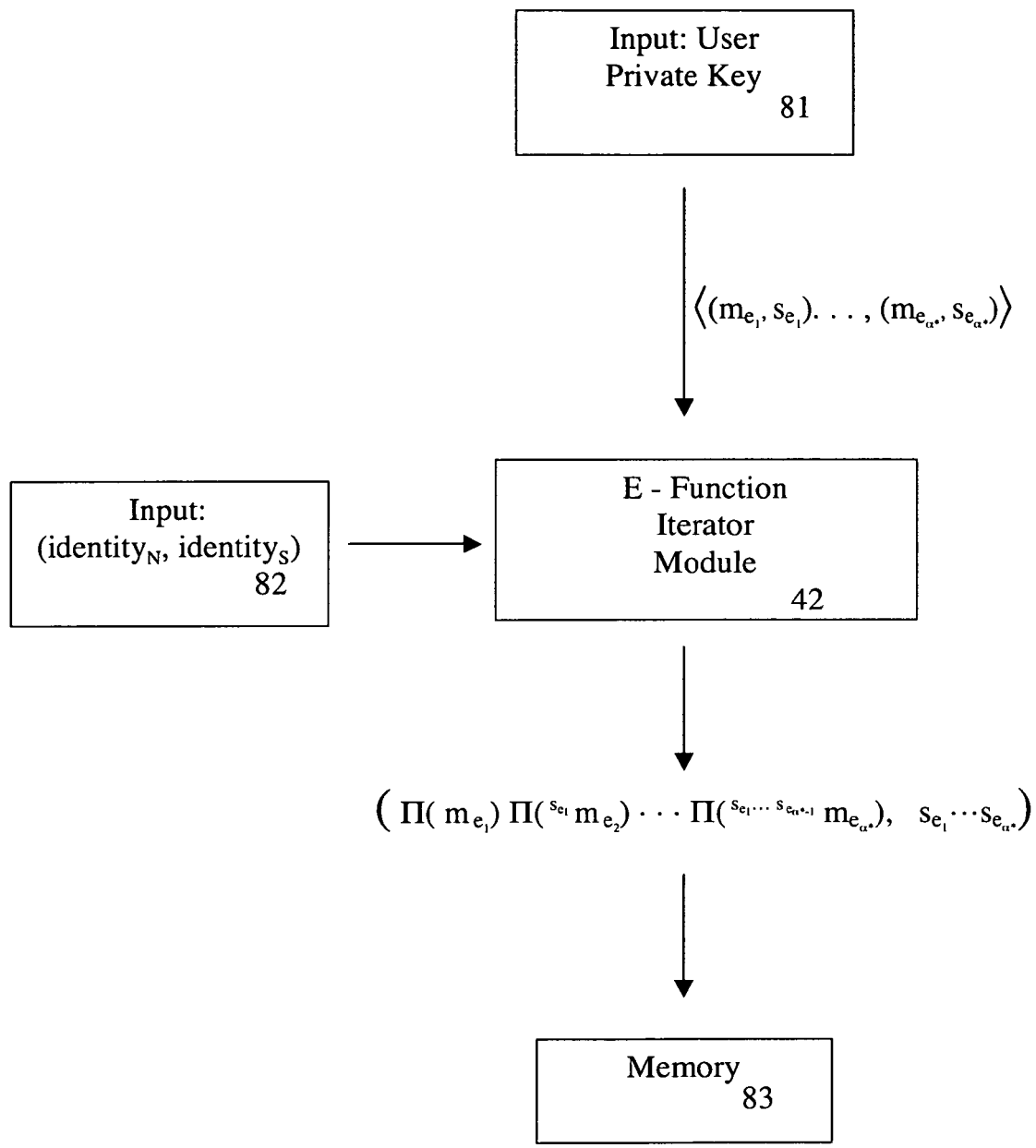
FIG. 8 is a system diagram illustrating a system for determining a public key in accordance with an embodiment of the invention.

Now that Alice and Bob have chosen their respective user private keys, FIG. 8 depicts the apparatus which may be used in computing the user public keys. The E-Function Iterator module 42 is responsive to the input $<(m_{e1}, s_{e1}), (m_{e2}, s_{e2}), \ldots, (m_{e_{\alpha^*}}, s_{e_{\alpha^*}})>$, 81 and the element $$(1_N, 1_S) = (identity_N, identity_S) \in N \times S,$$

which is the identity of the monoid N in the first component and the identity of S in the second component. The E-Function Iterator module 42 produces the User Public Key $$(N_A, s_A) = E((1_N, 1_S), (M_A, s_A))$$
$$= ((\Pi(m_{e_1})\Pi(^{s_1}m_{e_2}) \cdots \Pi(^{s_1 \cdots s_{\alpha^*-1}}m_{e_{\alpha^*}}), s_{e_1} \cdots s_{e_{\alpha^*}})$$
$$= (\Pi((m_{e_1})(^{s_1}m_{e_2}) \cdots (^{s_1 \cdots s_{\alpha^*-1}}m_{e_{\alpha^*}})), s_{e_1} \cdots s_{e_{\alpha^*}})$$
$$= (\Pi(M_A), s_A),$$

which is sent to memory 83.

Figure 9:
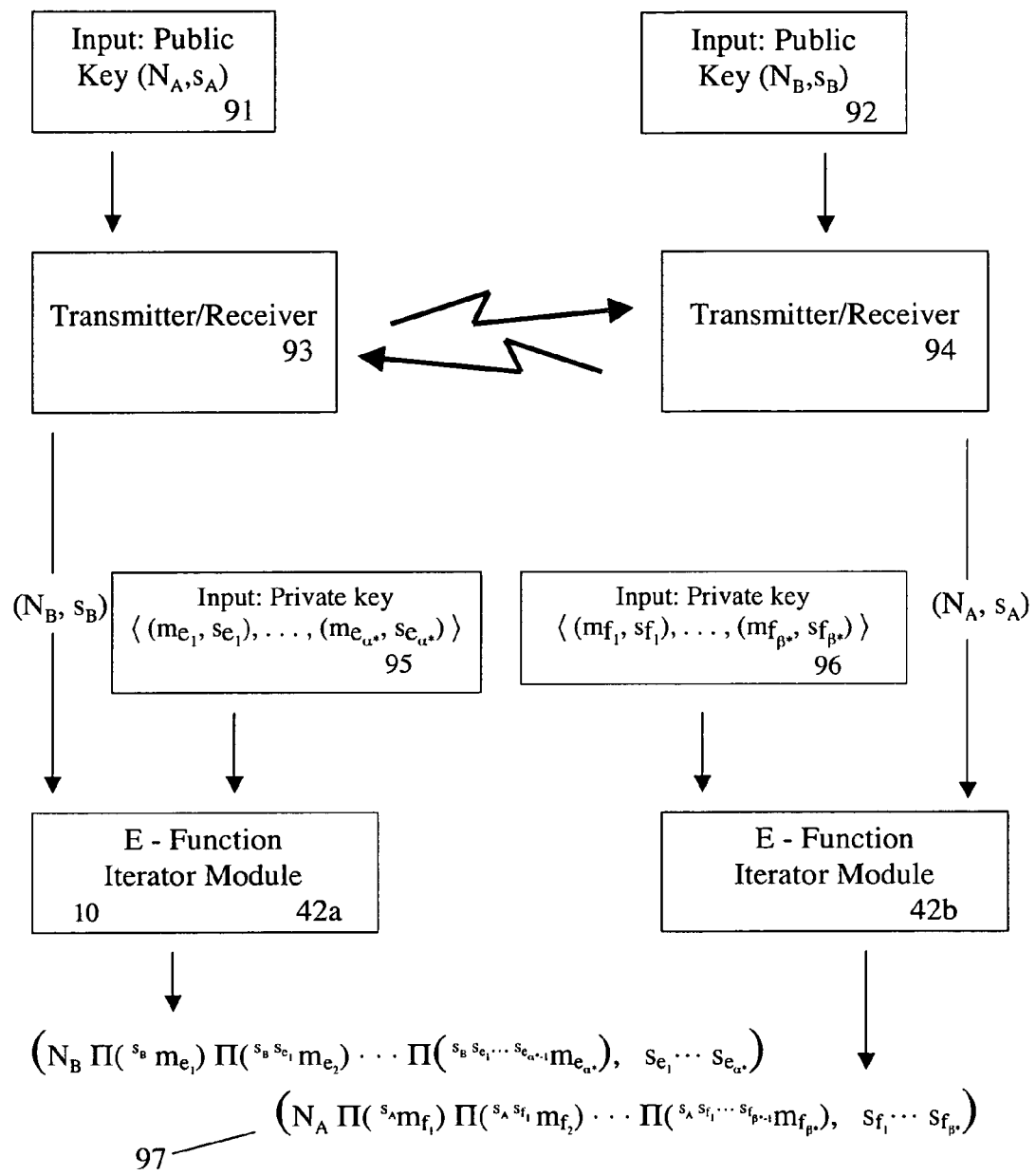
FIG. 9 is a system diagram illustrating a system for determining a common agreed upon secret key in accordance with an embodiment of the invention.

At this point Alice has the public key $(N_A, s_A)$ and private key $(M_A)$, Bob has public key $(N_B, s_B)$ and private key $<M_B>$, and they are now in a position to utilize the apparatus depicted in FIG. 9 to obtain a common agreed upon secret key. Alice transmits her public key $(N_A, s_A)$ input 91 via the transmitter/receiver 93, and likewise Bob transmits his public key $(N_B, s_B)$ input 92 via the transmitter/receiver 94. The received public keys together with the each users private keys are then forwarded to the respective E-Function Iterator modules 42a, 42b, to yield $$(N_B \Pi(^{s_B}M_A), s_B s_A) = E((N_B, s_B), (M_A, s_A)) = E((\Pi(M_B), s_B), (M_A, s_A))$$

$$(N_A \Pi(^{s_A}M_B), s_A s_B) = E((N_A, s_A), (M_B, s_B)) = E((\Pi(M_A), s_A), (M_B, s_B)).$$

Since $(M_A, s_A)$ and $(M_B, s_B)$ are contained in the submonoids $A_1, B_1$ respectively, the original assumptions regarding the structure of the algebraic eraser imply that the above elements of N×S are equal and can serve as the common agreed upon secret key, 97.

The above key agreement protocol can be enhanced by combining it with the Diffie-Hellman protocol described in the prior art. One such combination is given as follows. Referring to FIG. 8, replace input 82 by the element $(K_A, identity_S)$ (for Alice) and $(K_B, identity_S)$ (for Bob) where $K_A, K_B \in N$ are additional private keys chosen so that they commute. The public keys for Alice and Bob are, $E((K_A, identity_S), (M_A, s_A))$, $E((K_B, identity_S), (M_B, s_B))$, respectively. In this variation of the key agreement protocol, the common agreed upon secret key is given by $$E((K_A K_B \cdot \Pi(M_B), s_B), (M_A, s_A)) = E((K_B K_A \cdot \Pi(M_A), s_A), (M_B, s_B)).$$

Figure 11:
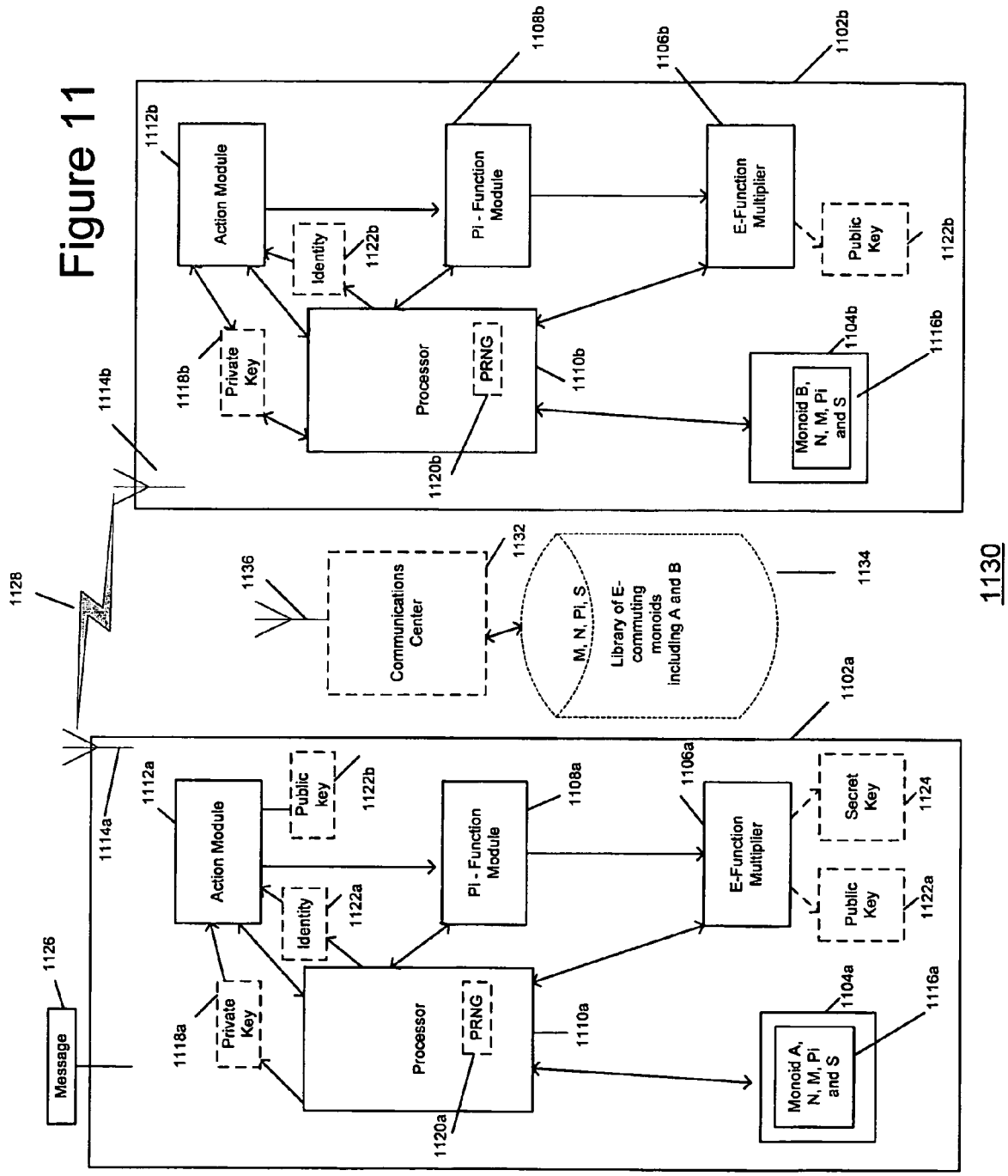
FIG. 11 is a system diagram illustrating a system for determining a secret key in accordance with an embodiment of the invention.

Referring now to FIG. 11, there is shown a system 1130 which could be used in accordance with an embodiment of the invention. System 1130 includes a first transmitter/receiver 1102a and a second transmitter/receiver 1102b. Transmitters/receivers 1102a and 1102b could be, for example, readers and tags in an RF-ID system. Transmitters/receivers 1102 and 1102b may, for example, generate information, receive information, or modulate received information to transmit other information.

Transmitter/receiver 1102a includes a memory 1104a, a processor 1110a, an action module 1112a, a Π-Function module 1108a an E-function multiplier 1106a and an antenna 1114a. Similarly, transmitter/receiver 1102b includes a memory 1104b, a processor 1110b, an action module 1112b, a Π-Function module 1108b, an E-function multiplier 1106b and an antenna 1114b. Action modules 1112a and 1112b could be, for example, S-action module 23 discussed above. Π-Function modules 1108a and 1108b could be, for example, Π-Function module 13 discussed above. E-Function multipliers 1106a and 1106b could be E-Function multipliers 35 as described above.

Memories 1104a and 1104b each include monoids N and M, group S and function Π which all could be determined using, for example, the algorithms discussed above. Memory 1104a further includes a submonoid A and memory 1104b further includes a submonoid B. Sub-monoids A and B may be determined as discussed above. For example, a semi-direct product of S and M may be determined. A and B may then be E-commuting submonoids of this semi-direct product. Monoids M and N, group S, function Π and submonoids A and B may all be determined by a communications center 1132 in communication with a database 1134. Communications center 1132 may forward monoids M and N, group S, function Π and sub-monoids A and B to transmitter/receivers 1102a, 1102b using, for example an antenna 1136. Alternatively, monoids M and N, group S, function Π and sub-monoids A and B, may be stored in memories 1104a, 1104 of transmitter/receives 1102a, 1102b respectively, when the respective devices are manufactured.

In operation, processors 1110a and 1110b each select generators of monoids A and B, respectively. The selection could be, for example, through the use a pseudo-random number generators 1120a, 1120b. Processor 1110a then orders the generators to produce a private key 1118a for transmitter/receiver 1102a.

Processor 1110a then forwards private key 1118a and an identity element 1122a to action module 1112a, Π-Function module 1108a and E-Function multiplier 1106a to produce a public key 1122a for transmitter/receiver 1102a. Identity element 1122a includes a first component which is the identity of monoid N and a second component which is the identity of group S. The process through action module 1112a, Π-Function module 1108a and E-Function multiplier 1106a may be performed iteratively for each generator in private key 1118a.

Similarly, processor 1110b orders generators of monoid B to produce a private key 1118b for transmitter/receiver 1102b. Processor 1110b then forwards private key 1118b and an identity element 1122b to action module 1112b, Π-Function module 1108b and E-Function multiplier 1106b to produce a public key 1122b for transmitter/receiver 1102b. Identity element 1122b includes a first component which is the identity monoid N and a second component which is the identity of group S. The process through action module 1112b, Π-Function module 1108b and E-Function multiplier 1106b may be performed iteratively for each generator in private key 1118b.

Transmitter/receivers 1102a and 1102b exchange their respective public keys 1122a, 1122b using antennas 1114a and 1114b respectively over a communication link 1128. Once the public keys 1122a, 1122b are received, a secret key may be ascertained. Focusing on transmitter/receiver 1102a, for example, public key 1122b from transmitter/receiver 1102b is input to action module 1112a, Π-function module 1108a and E-Function multiplier 1106a along with private key 1118a. Action module 1112a, Π-Function module 1108a, and E-Function multiplier 1106a may operate on these inputs iteratively for each generator in the private key from transmitter/receiver 1102a, to produce a secret key 1124. A similar operation is performed at transmitter/receiver 1102b. The secret key 1124 may be then be used by transmitter/receivers 1102a and 1102b to communicate securely.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modification are intended to be included within the scope of the invention.

EXAMPLE

An instance of the algebraic eraser and its associated key agreement protocol can be obtained in the case where the monoid. M is chosen to be the set of L×L matrices whose entries are rational functions with integral coefficients in the variables $\{t_1, t_2, \ldots, t_k\}$, i.e., the entries take the form $$\frac{C_{ij}(t_1, t_2, \ldots, t_k)}{D_{ij}(t_1, t_2, \ldots, t_k)}$$

where $1 \leq i, j \leq k$, and $C_{ij}, D_{ij}$ are polynomials. The group S is chosen to be the symmetric group on k symbols, denoted $S_k$. The action of the elements of $s \in S_k$ on the set of variables $\{t_1, t_2, \ldots, t_k\}$, given by $$s: t_i \to t_{s(i)},$$

can be extended to an action of the monoid M in a natural manner. Given an element of M, input 22, (see FIG. 2) of the form $$\left[\frac{C_{ij}(t_1, t_2, \ldots, t_k)}{D_{ij}(t_1, t_2, \ldots, t_k)}\right]_{1 \leq i, j \leq k}$$

and an element $s \in S_k$, input 21, the result of the $S_k$-Action module 23 is the element of M given by $$s\left[\frac{C_{ij}(t_1, t_2, \ldots, t_k)}{D_{ij}(t_1, t_2, \ldots, t_k)}\right]_{1 \leq i, j \leq k} = \left[\frac{C_{ij}(t_{s(1)}, t_{s(2)}, \ldots, t_{s(k)})}{D_{ij}(t_{s(1)}, t_{s(2)}, \ldots, t_{s(k)})}\right]_{1 \leq i, j \leq k}.$$

Having specified the monoid M and the action of a group S on M, we fix a prime p and let the monoid N be the set of L×L matrices whose entries are integers mod p. Then to define the homomorphism Π a set of integers $(T_1, T_2, \ldots, T_k)$ (mod p), is chosen and is stored in the Π-Function module Library 11. Given an element of M, Input 12, the Π-Function module produces the element of N given by $$\left[\frac{C_{ij}(\tau_1, \tau_2, \ldots, \tau_k) \bmod p}{D_{ij}(\tau_1, \tau_2, \ldots, \tau_k) \bmod p}\right]_{1 \leq i, j \leq k}.$$

It is tacitly assumed that $$D_{ij}(T_1, T_2, \ldots, T_k) \not\equiv 0 (\bmod p),$$

which can always be arranged by appropriate selection of $(\tau_1, \tau_2, \ldots, \tau_k)$ for the situation at hand.

With the above choices in place the E-Function 13 takes the form, $$E\left([d_{ij}], s\left(\left[\frac{C_{ij}(t_1, t_2, \ldots, t_k)}{D_{ij}(t_1, t_2, \ldots, t_k)}\right], s_1\right)\right) = \left([d_{ij}] \cdot \left[\frac{C_{ij}(\tau_{s(1)}, \tau_{s(2)}, \ldots, \tau_{s(k)}) \bmod p}{D_{ij}(\tau_{s(1)}, \tau_{s(2)}, \ldots, \tau_{s(k)}) \bmod p}\right], s \cdots_1\right).$$

The E-Function Iterator module 42 may be evaluated via the apparatus in FIG. 5.

A method for creating the library of pairs of E-Commuting monoids will now be specified. Each monoid in such a pair will be presented as a list of generators each of which is contained in M×S. A feature of the method is that the internal algebraic structure of the pairs of E-Commuting monoids is difficult to determine from the publicly announced list of generators. Choose two sets X, Y of elements of M, and two sets U, V of elements of $S_k$, where the following properties hold:

xy=yx uv=vu $^v x = x$ $^u y = y$, for all $x \in X$, $y \in Y$ and $u \in U$, $v \in V$. There are many such choices for the sets X,Y,U,V. In fact, the number of choices also grows exponentially with L.

One method to specifically choose the sets X,Y,U,V is given as follows. Partition the set $\{t_1, t_2, \ldots, t_k\}$ into two disjoint subsets $T_1, T_2$ where $T_i = \{t_{i_1}, t_{i_2}, \ldots, t_{i_k}\}$ for i=1,2. Correspondingly, there will exist two distinct subgroups U,V of $S_k$, where an element of U permutes the variables in $T_1$ and fixes the variables in $T_2$, and similarly an element of V permutes the variables in $T_2$ and fixes the variables in $T_1$. Observe that every element u ∈ U commutes with every element v ∈ V. Next choose positive integers $l_1$ and $l_2$ such that $L = l_1 + l_2 + 1$. The matrices in X are chosen to be of the form $$\begin{pmatrix} & & & 0 & & & \\ M_{\ell_1} & & & \vdots & & & \\ & & & 0 & & & \\ 0 & \cdots & 0 & 1 & 0 & \cdots & 0 \\ & & & 0 & 1 & & \\ & & & \vdots & & \ddots & \\ & & & 0 & & & 1 \end{pmatrix}$$

where $M_{l_1}$ is an $l_1 \times l_1$ matrix whose entries are rational functions in the variables $T_1$. All nonspecified entries the above matrix are equal to 0. Similarly, the matrices in Y are chosen to be of the form $$\begin{pmatrix} 1 & & & 0 & & & \\ & \ddots & & \vdots & & & \\ & & 1 & 0 & & & \\ 0 & \cdots & 0 & 1 & 0 & \cdots & 0 \\ & & & 0 & & & \\ & & & \vdots & & M_{\ell_2} & \\ & & & 0 & & & \end{pmatrix}$$

where $M_{l_2}$ is an $l_2 \times l_2$ matrix whose entries are rational functions in the variables $T_2$. It is clear that the above choices of matrices commute, and that an element u ∈ U acts trivially on each matrix in Y, and an element v ∈ V acts trivially on each matrix in X.

With this done choose an invertible element $(z,w) \in M \times S$. There are many such choices for (z,w), and in fact, the number of such choices grows exponentially with L. One can now define the submonoids as $A = \{(z,w) \cdot (x,u) \cdot (z,w)^{-1} | x \in X, u \in U\},$ $B = \{(z,w) \cdot (y,v) \cdot (z,w)^{-1} | y \in Y, v \in V\}.$ It is readily verifiable that A, B are E-Commuting monoids. Note that the search for (z,w) is more difficult than a standard conjugacy search problem because the conjugated elements are unknown.

In the key agreement protocol, there are two users, Alice and Bob, each of whom has a public and a private key. The users proceed with a public exchange, after which each is in a position to obtain common agreed upon secret key which can then be used for further cryptographic applications. The key agreement protocol begins in this example with each user, Alice and Bob, being assigned a user submonoid $A_1$, and $B_1$, respectively, from a pair in the E-Commuting Monoid Library, 63. Each user, Alice and Bob, proceeds to choose a private key which is the output of a respective Private Key Generator 74. Each user public key is then computed by directing the user private key, input 81 to the E-Function Iterator module 42, along with the input 82. The E-Function Iterator module 42 allows the users to compute their respective public keys in a novel and rapid fashion. The computations involved are 8-bit modular arithmetic operations (addition, subtraction, multiplication, and division) and 8-bit string search and replacement. These computations can be achieved at low cost and high efficiency.

Finally, the public keys are exchanged via the transmitter/receivers 93, 94. The results of this exchange, along with the users private keys, are sent to the E-Function Iterator module 42*a*, 42*b*, which outputs the common agreed upon secret key 97.

What is claimed is:

1. A transmitter comprising:
    a memory including a first submonoid, the first submonoid being produced by:
        selecting a first monoid;
        selecting a second monoid;
        selecting a function, the function being a monoid homomorphism that maps
    the first monoid to the second monoid;
        selecting a group;
        selecting an action of the group on the first monoid; and
        determining a semi-direct product of the first monoid and the group to produce a third monoid;
        selecting a first and second submonoid of the third monoid, the pair of the first and second submonoids satisfying a criterion, the first submonoid being defined by a first set of generators, the criterion satisfying a property determined by the function, a structure of the first and second monoids, and the action;
    and a processor; wherein
    the processor is effective to select a plurality of generators of the first set of generators to produce a private key,
    the processor is effective to apply the second component of an identity on a non-group component of a first generator of the private key to produce a result, wherein the identity comprises a first component, the first component being an identity of the second monoid, and the identity comprises a second component, the second component being an identity of the group;
    the processor is effective to apply the function to the result to produce a first modified result;
    the processor is effective to multiply the first component of the identity by the modified result to produce a first further modified result;
    the processor is effective to multiply the second component of the identity with a group component of the first generator to produce a first still further modified result; and
    the processor is effective to combine the first further modified result with the first still further modified result to produce a first public key;
    the processor is effective to:
        a. apply a group component of the first public key on a non-group component of a second generator of the private key to produce a second result;
        b. apply the function to the second result to produce a second modified result;
        c. multiply a non-group component of the first public key by the second modified result to produce a second further modified result;
        d. multiply the group component of the first public key with a group component of the second generator of the private key to produce second still further modified result; and e. combine the first further modified result with the second still further modified result to produce a second public key.

2. The transmitter as recited in claim 1, wherein the processor is further effective to iteratively perform a through e for all the generators in the first private key.

3. A system for securing communications between users, the system comprising:
a communications center, the communications center effective to:
   select a first monoid;
   select a second monoid;
   select a function, the function being a monoid homomorphism that maps the first monoid to the second monoid;
   select a group;
   select an action of the group on the first monoid;
   determine a first semi-direct product of the first monoid and the group to produce a third monoid; and
   select a first and second submonoid of the third monoid, a pair of the first and second submonoids satisfying a criterion, the first submonoid being defined by a first set of generators, the second submonoid being defined by a second set of generators, the criterion satisfying a property determined by the function, a structure of the first and second monoids, and the action;
a first transmitter comprising:
   a memory including the first submonoid;
   a first processor, the first processor effective to:
      select a plurality of generators of the first set of generators to produce a first private key;
      apply the second component of an identity on a non-group component of a first generator of the first private key to produce a first result, wherein the identity comprises a first component, the first component being an identity of the second monoid, and the identity comprises a second component, the second component being an identity of the group;
      apply the function to the first result to produce a first modified result;
      multiply the first component of the identity by the modified result to produce a first further modified result;
      multiply the second component of the identity with a group component of the first generator to produce a first still further modified result; and
      combine the first further modified result with the first still further modified result to produce a first public key;
   the first processor is further effective to
      a. apply a group component of the first public key on a non-group component of a second generator of the private key to produce a second result;
      b. apply the function to the second result to produce a second modified result;
      c. multiply a non-group component of the first public key by the second modified result to produce a second further modified result;
      d. multiply the group component of the first public key with a group component of the second generator of the first private key to produce second still further modified result; and
      e. combine the first further modified result with the second still further modified result to produce a second public key;
a second transmitter comprising:
   a memory including the second submonoid;
   a second processor, the second processor effective to
      select a plurality of generators of the second set of generators to produce a second private key;
      apply the second component of the identity on a non-group component of a first generator of the second private key to produce a third result,
      apply the function to the third result to produce a third modified result;
      multiply the first component of the identity by the third modified result to produce a third further modified result;
      multiply the second component of the identity with a group component of the second generator to produce a third still further modified result;
      combine the third further modified result with the third still further modified result to produce a third public key;
   the second processor is further effective to:
      f. apply a group component of the third public key on a non-group component of a second generator of the second private key to produce a fourth result;
      g. apply the function to the fourth result to produce a fourth modified result;
      h. multiply a non-group component of the first public key by the fourth modified result to produce a fourth further modified result;
      i. multiply the group component of the third public key with a group component of the second generator of the second private key to produce fourth still further modified result; and
      j. combine the fourth further modified result with the fourth still further modified result to produce a fourth public key.

4. The system as recited in claim 3, wherein:
the second processor is further effective to forward the fourth public key to the first processor; and
the first processor is further effective to:
   apply a group component of a first element of the fourth public key on a non-group component of the first private key to produce a fifth result;
   apply the function to the fifth result to produce a fifth modified result;
   multiply a non-group component of the first element of the fourth public key by the fifth modified result to produce a fifth further modified result;
   multiply the group component of the fourth public key with a group component of the first generator of the first private key to produce a fifth still further modified result; and
   combine the fifth further modified result with the fifth still further modified result to produce a first secret key,
   k. apply a group component of the first secret key on a non-group component of a second generator of the first private key to produce a sixth result;
   l. apply the function to the sixth result to produce a sixth modified result;
   m. multiply a non-group component of the first secret key by the sixth modified result to produce a sixth further modified result;
   n. multiplying the group component of the first secret key with a group component of the second generator of the private key to produce a sixth still further modified result; and o. combining the sixth further modified result with the sixth still further modified result to produce a second secret key.

5. The system as recited in claim 4, further comprising repeating steps a through e for all generators of the first private key.

6. The system as recited in claim 5, further comprising repeating steps f through j for all generators of the second private key.

7. The system as recited in claim 6, further comprising repeating steps k through o for all generators of the first private key.

8. The system as recited in claim 7, further comprising encrypting a message using, at least in part, the second secret key.

* * * * *